United States Patent [19]
Ray

[11] Patent Number: 6,124,108
[45] Date of Patent: Sep. 26, 2000

[54] PROTEIN BIOMARKER FOR MUSTARD CHEMICAL INJURY

[75] Inventor: Prabhati Ray, Potomac, Md.

[73] Assignee: The United States of America as represented by the Secretary of the Army, Washington, D.C.

[21] Appl. No.: 08/855,268

[22] Filed: May 13, 1997

Related U.S. Application Data

[60] Provisional application No. 60/017,913, May 15, 1996.
[51] Int. Cl.7 .................................................. G01N 33/573
[52] U.S. Cl. ............................ 435/7.4; 435/212; 530/412
[58] Field of Search ..................... 435/7.4, 212; 530/412

[56] References Cited

U.S. PATENT DOCUMENTS 4,343,734   8/1982   Lian et al. ............................... 260/112

*Primary Examiner*—James C. Housel
*Assistant Examiner*—Quang N Phan
*Attorney, Agent, or Firm*—Charles H. Harris; John Francis Moran

[57] ABSTRACT

This invention relates to the discovery that toxicity to mustard may be evaluated by diagnostic test means disclosed herein. Upon electrophoretic separation (sodium dodocyl sulfate polyacryl-amide gel electrophoresis (SDS-PAGE)) of buffered extract of human skin cells (normal human epidermal keratinocytes (NHEK)) which had been exposed to mustard-type chemical compounds a band at approximately 50,000 to 80,000 daltons molecular weight was found. The protein band constitutes a biomarker. The marker protein can be used either to raise protective antibodies to protect against the protease or may be used in a kit for identifying presence or absence of the marker in study of tissues taken from individuals who may have been exposed to mustard poisoning.

2 Claims, No Drawings

PROTEIN BIOMARKER FOR MUSTARD CHEMICAL INJURY

This application relies on Provisional Patent Application 60/017,913 filed May 15, 1996.

FIELD OF THE INVENTION

This invention relates to the use of a test to evaluate exposure to mustard gas. The invention provides methods and a kit for use in evaluating exposure and response to mustard.

BACKGROUND OF THE INVENTION

The use of sulfur mustard, bis-(2-chloroethyl) sulfide (HD) in chemical warfare has been long known. More recently its use in the Iran-Iraq conflict resulted in many deaths and untold suffering. It's use was a major threat in the Gulf War. Hence, the method of identifying injury due to mustards is an important pursuit for scientists working for the armed forces.

It is believed that nitrogen and sulfur mustard-induced vesication wherein there is separation of the epidermis from the dermis due to the disruption of the connective tissues may be the result of a specific protease. The exact mechanism of its toxicity remains unclear and no effective antidote has yet been reported in the literature. DNA is considered to be its major intracellular target (Papirmeister et al., 1985). Other toxic effects are protease stimulation, cutaneous degradation and blister formation. Smith et al. (1991) and Cowan et al. (1991) have demonstrated that HD and another vesicating agent chloroethylethyl sulfide (CEES) stimulate protease activity in NHEK, Hela Cell line and in human peripheral blood lymphocytes. No information, however, exists with respect to the molecular mechanism of mustard-induced protease activation.

Immunohistochemical studies have been done on the protein composition changes in HD-exposed hairless guinea pig skin. Epidermal-dermal junction proteins, namely, bullous pemphigoid antigen, laminin and hemidesmosomal anchoring filament proteins were affected by exposure to HD. More recently, investigators have found that in the mini pig skin, which is more akin to human skin, only one protein in the lamina lucida, thelamini, is affected by HD. These findings strongly suggest that some specific protease(s) may be responsible for HD-induced vesication.

The concept that a specific protease is involved in pathology related to exposure to mustards is important because the use of generalized protease inhibitors could cause serious side-effects. Cowman, et al. have demonstrated that HD and chloroethyl ethyl sulfide (CEES) stimulate protease activity in vitro in human peripheral blood lymphocytes and in vivo in hairless guinea pig skin. However, a definitive characterization of the mustard-stimulated protease is not described in any previous publication.

SUMMARY OF THE INVENTION

This invention relates to a protease which can be stimulated by exposure of NHEK cells to mustard in the presence of $Ca^+$ wherein proteolytic activity is inhibited by leupeptin at 1 mM concentration but is not inhibited by pepstatin at 1 mM concentration.

DESCRIPTION OF THE INVENTION

This invention relates to the discovery that toxicity to mustard may be evaluated by diagnostic test means disclosed herein.

Upon electrophoretic separation (sodium dodocyl sulfate polyacrylamide gel electrophoresis (SDS-PAGE))of buffered extract of human skin cells (normal human epidermal keratinocytes (NHEK)) which had been exposed to mustard-type chemical compounds a band at approximately 50,000 to 80,000 daltons molecular weight was found. (The position of the band was determined partly by the % of polyacrylamide gel used, with the band being between 65% and 80% when 12.5% concentration of the gel was used and lower when the 10% gel was used). This new protein was seen in mustard-exposed NHEK, in pig skin, and in skin of hairless mice. The mustard compounds used included chloroethyl ethyl sulfide (CEES) and 2-chloro-N-(2-chloroethyl)-N-methylethanamine hydrochloride, also known as nitrogen mustard ($HN_2$). The protein band from NHEK cultures had protease activity that was identical to characteristics of protease stimulated by mustard. Bis-2-chloroethyl sulfide (HD), also known as sulfur mustard, may also be used in similar manner.

The protein band constitutes a biomarker. The marker protein can be used either to raise protective antibodies to protect against the protease or may be used in a kit for identifying presence or absence of the marker in study of tissues taken from individuals who may have been exposed to mustard poisoning.

At present, pathological changes resulting from mustard poisoning are identified by histopathologic and electron microscopic means. The instant invention provides more economical and efficient means of identifying mustard-related pathologies. The improved diagnostic tests make it possible to treat such pathologies more expeditiously.

Materials and Methods

An in vitro normal human epidermal keratinocytes (NHEK) model was used to study and characterize protease stimulated by some common mustards, including 1-chlorethyl ethyl sulphide (CEES) and 2-chloro-N-(2 chloroethyl)-N-methylethanamine hydrochloride ($HN_2$). These cells provide an appropriate human non-tumor primary skin cell culture model which makes it possible to perform the experimental manipulations necessary to study the effect of vesicants.

CEES was obtained from Aldrich Chem. Milwaukee, Wis. $HN_2$ was purchased from Merck & Co. West Point, Pa. NHEK stock culture was purchased from Clonetics Corp. San Diego, Calif. Sulfur mustard (HD)-exposed NHEK sample was obtained from USMRICD, APG, MD. The peptide substrate TRY (carbobenzoxy-valyl-glycl-arginine-4-nitraline acetate) was obtained from Boehringer Mannheim Biochemical in Indiana. Protease inhibitors diisopropyl fluoro phosphate (DFP), phenylmethyl sulfonylfluoride (PMSF), leupeptin, E-64 and pepstatin were purchased from Signa Chemical Company in Missouri.

The in vitro normal human epidermal keratinocytes

Cell culture

Secondary cultures of (NHEK) were grown up to 100% plus confluence as described previously (Mol et al., 1989). Cells were exposed to different concentrations of CEES and $HN_2$ at ambient conditions of incubation in a humidified atmosphere of 5% $CO_2$/95% air at 37° C. for 24 hours.

It has been possible to identify vesicant-induced proteases. Using the methods of the invention, it is also possible to demonstrate and test protectants against the offending protease.

Chromogenic Peptide Substrate Protease Assay (CPSPA). This assay was performed using chromozym TRY substrate (2.5 mM) following the method of Friberger (1982) as described by Smith and Cowan (Cell Biol.Toxicol. 7, 238–248 (1991)). The chromogenic peptide, when cleaved by protease, releases p-nitroaniline (pNA) producing a change in absorbance measured spectrophotometrically at 405 nm. The findings obtained by chromogzym (TRY) peptide substrate protease assay (CPSPA) revealed the optimum mustard concentration and time for protease stimulation to be about 200 $\mu$M CEES or 100 $\mu$M HN$_2$ over about 16 hours.

Using the methods of the invention, it has been possible to detect an tissue injury-related protease. Both colorimetric and electrophoretic assays are disclosed.

The chromogenic peptide substrate protease assay (CPSPA) of Cowan, (1991) was practiced in order to reproduce Cowan's work on the observation of vesicant-induced protease stimulation by studying the effects of both CEES and HN$_2$ in NHEK. Mustard-induced protease stimulation was found only with the trypsin-specific substrate. This indicated that mustards may stimulate serine protease(s).

SDS-PAGE

To identify mustard-stimulated protease, SDS-polypeptide complexes were separated by SDS-PAGE on 10% to 12.5% polyacrylamide gel. Mustard-treated cells were solubilized in sample buffer and boiled for 5 minutes at 95° C. Several protease inhibitors were included during the wash and after solubilization using the protease inhibitor sampler kit, P6548, from Molecular Probes, Eugene, Oreg., U.S.A. following the instructions therewith. Densitometric analysis was done in the form of arbitrary optical density units (Bio-Med Instruments). Western blot analysis was done using rabbit anti-keratine wide spectrum screening primary antibody and peroxidase-conjugated swine immunoglobins to rabbit immunoglobins as secondary antibody. To demonstrate protease activity in the ≅50 to ≈80 kDa band, proteins in the cell extract were separated by Non-SDS-PAGE and then the band was eluted in phosphate buffer at 37 C.

EXAMPLE 1

Effect of different mustard concentrations on protease stimulation

NHEK were exposed to different concentrations of mustards and kept for 24 hours. Protease stimulation was determined after 16 hours incubation with chromozym substrate. The results demonstrated concentration-dependent increase in protease stimulation up to 200 $\mu$M for CEES and 100 $\mu$M for HN$_2$ followed by a decrease.

A peptag gel electrophoresis assay was used to detect protease action. This assay is based on the differences in electrophoretic mobility of dye-linked peptide substrates which show changes in net electric charge and molecular weight because of alteration which is dependent on the site of protease action. The nature of the protease can be determined by comparing the results found when test proteases are compared with results found when known, commercially available proteases and substrates are used for comparison. The assay has been used to detect less than 100 pg of tryptic and chymotryptic-like proteases. Data obtained by this method confirmed the CPSPA finding that mustard stimulates serine protease.

EXAMPLE 2

Time dependence of mustard-induced protease stimulation

NHEK were exposed to 200 $\mu$M CEES and 100 $\mu$M HN$_2$ for 24 hours. Protease stimulation was determined at different time points. These results indicate a marked protease stimulation in mustard treated cells compared to control at 8 and 16 hour: 8 to 10 fold increase over the CEES treated cells, and a 12 to 16 fold increase in HN2 treated cells.

EXAMPLE 3

Characterization of mustard-stimulated protease

NHEK were exposed to 200 $\mu$M CEES and kept for 24 hours. Protease stimulation after 16 hours of incubation with chromozym substrate in the presence of 0.15 mM Ca$^{2+}$ was significantly (p<0.0001) higher than the control cell. However this stimulation was completely inhibited by adding calcium chelator EGTA (2 mM), or serine protease inhibitor DFP (1 mM), or protein synthesis inhibitor cycloheximide (35$\mu$M) in the extracellular medium.

EXAMPLE 4

Effect of mustards on NHEK membrane proteins (SDS-PAGE)

Coomassie blue staining showed a visible band in both CEES (200 $\mu$M) and HN$_2$ (100 $\mu$M)-exposed NHEK. Densitometeric analysis showed the intensity of this band to be about 4-fold greater for CEES and about 6-fold greater for HN$_2$-exposed cells than the control samples.

EXAMPLE 5

Characterization of mustard-stimulated protein eluted from non-SDS-PAGE gel

NHEK were exposed to 200 $\mu$M HN$_2$ and 300 $\mu$M HD respectively and kept for 24 hours. Mustard stimulated protein band from 12.5% non-SDS-PAGE was eluted and the protease was determined after incubation with the substrate by CPSPA at different time points. The results indicate a significant (p<0.0001) protease stimulation after 16 hours incubation. This band corresponded to the protein on SDS-PAGE.

EXAMPLE 6

Effect of different HD concentrations on protein stimulation (SDS-PAGE)

NHEK were exposed to different concentrations of HD and kept for 24 hours. Cell extracts were analyzed by 12.5% SDS-PAGE. Coomassie blue staining indicated a band which was most prominent at 300 $\mu$M HD. This concentration was therefore considered to be the optimum for HD stimulation of the KDa protein band. The decrease in intensity at 1 mM HD was consistent with the decrease in mustard-stimulated protease at 1 mM.

EXAMPLE 7

Effect of EGTA on HD-induced protein band stimulation (SDS-PAGE)

NHEK were exposed to 300 $\mu$M sulfur mustard and kept for 24 hours. Cell extract analyzed by 12.5% SDS-PAGE showed stimulation of a protein band, which was inhibited by the presence of calcium chelator EGTA (2 mM) in the extracellular medium prior to and during HD exposure. These results indicate that this protein could be the mustard stimulated Ca$^{2+}$-dependent protease.

EXAMPLE 8

Protease activity was measured in different subcellular fraction

Mustard-induced protease was associated with the 105,000 g cell pellet. Sub-cellular fractions were prepared from NHEK at 24 hours after exposure to 200 μM CEES. Mustard increased protease was observed after 16 hours of incubation with chromozym substrate in both 1500 g and 105,000 g pellets, but not in the supernatant fractions. The protease stimulation was dependent on $Ca^{2+}$. (See Table 1.)

TABLE 1

| Sub-cellular Fractions | Treatment | Protease stimulation (% of control) |
|---|---|---|
| 1500 g Pellet | None | 157.75 ± 2.65 |
|  | CEES + 0.15 mM $Ca^{2+}$ | 1309.25 ± 26.61 |
|  | CEES + EGTA + BAPTA | 159.75 ± 3.08 |
| 1500 g Supernatant | None | 156.00 ± 3.60 |
|  | CEES + 0.15 mM $Ca^{2+}$ | 177.25 ± 1.50 |
|  | CEES + EGTA +− BAPTA | 155.21 ± 0.40 |
| 105,000 g Cytosol | None | 165.62 ± 11.83 |
|  | CEES + 0.15 mM $Ca^{2+}$ | 161.50 ± 1.50 |
|  | CEES + EGTA +− BAPTA | 160.25 ± 6.71 |
| 105,000 g Pellet | None | 194.87 ± 10.18 |
|  | CEES + 0.15 mM $Ca^{2+}$ | 1837.25 ± 26.63 |
|  | CEES + EGTA +− BAPTA | 160.50 ± 2.90 |

It was found that there was a time dependence on protease stimulation in mustard-treated NHEK. Protease stimulation increased significantly at all time points when assayed after incubation with chromozyme TRY substrate from 1 hour to 16 hours followed by a decrease in 24 hours. At 16 hours post-exposure maximal stimulation was found.

I claim:

1. A method of identifying a mustard-stimulated protease in a sample comprising the steps of:

1) separation of the sample on 10% to 12% non-SDS-PAGE gel, 2) extraction of a protein band found at about 80 kDa, 3) elution of the protein band extracted in step 2, 4) preparation of a pellet from the elute of step 3, 5) solubilizing the pellet obtained in step 4, 6) exposing the product of step 5 to antibodies against known mustard-stimulated protease, and 7) evaluating the product of step 6 to determine whether or not antibodies of step 6 have bound to a protease wherein binding is indicative of protease in the sample.

2. A method of claim 1 wherein the pellet in step 4 is prepared using centrifugation at about 1500 g.

* * * * *